United States Patent [19]

Scheuffgen et al.

[11] 4,292,088
[45] Sep. 29, 1981

[54] BEESWAX SUBSTITUTE

[75] Inventors: Ingeborg Scheuffgen, Neuss; Uwe Ploog, Haan, both of Fed. Rep. of Germany

[73] Assignee: Henkel Kommanditgesellschaft auf Aktien, Düsseldorf-Holthausen, Fed. Rep. of Germany

[21] Appl. No.: 102,266

[22] Filed: Dec. 10, 1979

[30] Foreign Application Priority Data

Dec. 27, 1978 [DE] Fed. Rep. of Germany ....... 2856277

[51] Int. Cl.$^3$ ...................... A61K 7/00; A61K 7/025; C08L 91/06; C08L 91/08
[52] U.S. Cl. ................................... 106/268; 106/270; 106/271; 424/64; 424/365
[58] Field of Search ............... 106/268, 270, 271, 245; 424/65; 426/365

[56] References Cited

U.S. PATENT DOCUMENTS 2,385,849 10/1945 Snell et al. .......................... 106/270
3,914,131 10/1975 Hutchinson ........................ 106/268

Primary Examiner—Allan Lieberman
Attorney, Agent, or Firm—Hammond, Littell, Weissenberger and Muserlian

[57] ABSTRACT

This invention is directed to a substitute beeswax composition comprised of:
mono-, di-, and triglycerides of long-chain fatty acids;
esters of long-chain fatty acids with higher-molecular fatty alcohols;
higher fatty acids;
optionally microcrystalline paraffins; and
from about 3 to 15% by weight, based on the weight of the total composition, of α-branched, aliphatic monocarboxylic acids of the general formula

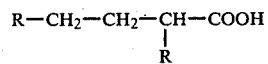

in which R represents a linear alkyl radical with from about 12 to 20 carbon atoms. The substitute beeswax composition is useful in the preparation of cosmetic compositions.

8 Claims, No Drawings

BEESWAX SUBSTITUTE

FIELD OF INVENTION

This invention relates to a substitute for beeswax. More particularly, this invention relates to a novel composition comprised of mono-, di-, and triglycerides of long-chain fatty acids, esters of long-chain fatty acids with higher-molecular alcohols, higher fatty acids, microcrystalline paraffins, and higher-molecular α-branched, aliphatic monocarboxylic acids.

BACKGROUND OF THE INVENTION

Beewax is a term employed to describe wax from the honeycomb of the bee. Due to its diverse favorable properties, beewax has found application in the field of cosmetics in cremes, make-up, lipsticks, emulsions, ointments, depilatories, and similar products. The shortage of beewax and its consequent extension and adulteration, which lead to great fluctuations in quality, have given rise to the desire for an equivalent substitute. The results of respective efforts so far could never do justice to more than part of the properties of beeswax, and the demand for a substitute coming very close to beewax in its entirety has remained.

OBJECTS OF THE INVENTION

It is an object of this invention to provide a substitute for beeswax.

It is also an object of this invention to provide a substitute for beeswax that is suitable for use in cosmetic preparations.

These and other objects of the invention will become more apparent in the discussion below.

DESCRIPTION OF THE INVENTION

It has now been found that a beeswax substitute with properties comparable to those of natural beeswax can be prepared. This beeswax substitute comprises a basic combination of mono-, di-, and triglycerides of long-chain fatty acids, esters of long-chain fatty acids with higher-molecular alcohols, higher fatty acids, and microcrystalline paraffins, as well as from about 3 to 15% by weight, preferably from about 3 to 8% by weight, of α-branched, aliphatic monocarboxylic acids of the general formula

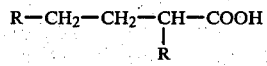  (I)

in which R represents a linear alkyl radical with from about 12 to 20, preferably from about 14 to 16, carbon atoms.

The compositions according to the invention preferably represent mixtures of (a) from about 3 to 15% by weight of the α-branched, aliphatic monocarboxylic acids of Formula I;

(b) from about 15 to 30% by weight of esters of fatty alcohols of the chain lengths $C_{12}$–$C_{22}$, preferably $C_{14}$–$C_{20}$, and fatty acids of the chain lengths $C_{14}$–$C_{22}$, preferably $C_{16}$–$C_{20}$;

(c) from about 5 to 20% by weight of triglycerides of palmitic, stearic, hydroxystearic, or behenic acid;

(d) from about 20 to 40% by weight of mono- and/or diglycerides of palmitic, stearic, hydroxystearic, or behenic acid;

(e) from about 5 to 20% by weight of fatty acids or hydroxy fatty acids of the chain lengths $C_{16}$–$C_{22}$; and (f) from 0 to about 30% by weight of microcrystalline paraffins having a melting range of from about 70° to 72° C.

Compositions particularly suitable for the purposes of the invention are comprised as follows:

(a) from about 3 to 8% by weight of the α-branched, aliphatic monocarboxylic acids of Formula I;

(b) from about 20 to 30% by weight of esters of fatty alcohols of the chain lengths $C_{14}$–$C_{20}$ and fatty acids of the chain lengths $C_{16}$–$C_{20}$;

(c) from about 10 to 15% by weight of triglycerides of palmitic, stearic or hydroxystearic acid;

(d) from about 20 to 40% by weight of monoglycerides of palmitic, stearic, or hydroxystearic acid;

(e) from about 10 to 20% by weight of fatty acids or hydroxy fatty acids of the chain lengths $C_{18}$–$C_{20}$; and (f) from about 10 to 20% by weight of microcrystalline paraffins having a melting range of from about 70° to 72° C.

A most preferred embodiment of the invention, having the most favorable properties, is a composition comprising of:

(a) about 5% by weight of α-branched, aliphatic monocarboxylic acids of Formula I, in which R represents a linear alkyl radical with from about 14 to 16 carbon atoms;

(b) about 25% by weight of cetyl palmitate;

(c) about 10% by weight of glyceryl trihydroxystearate;

(d) about 30% by weight of glyceryl monohydroxystearate;

(e) about 10% by weight of 12-hydroxystearic acid; and (f) about 20% by weight of microcrystalline paraffin having a melting range of from about 70° to 72° C.

These above-mentioned compositions, particularly the last-mentioned one, very closely resemble natural beeswax of DAB 7 quality (German Pharmacopoeia, Edition 1968) with respect to the analytical data as well as their behavior in respective cosmetic preparations. The α-branched, aliphatic monocarboxylic acid, or the mixture of α-branched, aliphatic monocarboxylic acids, is to be regarded as a major component that determines the quality of the compositions.

The α-branched, aliphatic monocarboxylic acids of Formula I suitable for the preparation of beeswax substitute compositions according to the invention can advantageously be prepared according to the British Pat. No. 1 462 228, incorporated herein by reference, by the following procedure:

(i) dimerizing in a well-known manner linear primary alkanols of the formula

  (II)

in which R represents a radical with from about 12 to 20, preferably from about 14 to 16 carbon atoms, to α-branched alcohols of the formula

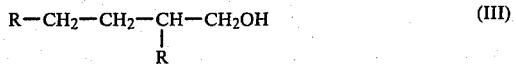  (III)

in which R is as defined above;

(ii) converting the α-branched alcohol of Formula III obtained into the alkali metal salt of the corresponding α-branched, aliphatic monocarboxylic acid by oxidative alkaline fusion; and (iii) setting the α-branched, aliphatic monocarboxylic acid free from the alkali metal salt by acidifying with mineral acid or another acid.

Starting alcohols for the preparation of the α-branched, monocarboxylic acids include myristyl alcohol, pentadecyl alcohol, cetyl alcohol, stearyl alcohol, nonadecyl alcohol, eicosyl alcohol, and behenyl alcohol, as well as their mixtures that can be obtained from natural mixtures of fatty acids.

Useful microcrystalline paraffins, i.e., microwaxes, include, for example, Microwachs HP 67, which is available from Erste Süddeutsche Ceresinfabrik Georg Schütz, Oberursel 5, West Germany.

For the preparation of the beeswax substitute composition, the individual components are cautiously melted together in such a manner to prevent localized overheating or burning. The mass of waxy material obtained in this manner can be used instead of beeswax in the usual manner in cosmetic preparations such as skin cremes, lipsticks, creme emulsions, and the like. Other regular components in such cosmetic preparations, such as emulsifying agents, fats, vaseline, paraffin oil, glycerine, vitamins, plant extracts, preservatives, and dyes, can be processed together with the beeswax substitute according to the invention without difficulties. Products are obtained that do not differ significantly from those prepared with beeswax.

The following examples are intended to illustrate the subject of the invention but are not to be construed as limiting the invention thereto.

EXAMPLES

Preparations of the α-Branched Aliphatic Monocarboxylic Acids

α-Branched fatty alcohols serving as intermediates were prepared in the following manner:

Approximately 5 mols of the starting alcohol were slowly heated with 25 gm of 50% potassium hydroxide solution, 0.2 gm of iron(III)-sulfate, and 0.1 gm of copper sulfate, under a stream of nitrogen, to approximately 300° C., and the mixture was maintained at this temperature until water no longer separated. The crude product was washed until it was free from alkali, dired, and separated by distillation from the unconverted starting alcohol. The following α-branched fatty alcohols (Guerbet fatty alcohols) were prepared by this method:

I. Guerbet fatty alcohol $C_{28}$

Hydroxyl number—136
Iodine number—2.5
Starting alcohol—n-tetradecanol-1.

II. Guerbet fatty alcohol $C_{32/36}$

Hydroxyl number—106
Iodine number—5
Melting point—34.5° C.
Starting alcohol—1:1 mixture of n-hexadecanol-1 and n-octadecanol-1

III. Guerbet fatty alcohol $C_{44}$

Hydroxyl number—87
Iodine number—2.5
Starting alcohol—n-docosanol-1.

For the preparation of the corresponding α-branched, aliphatic monocarboxylic acid (Guerbet fatty acids), the Guerbet fatty alcohols were heated to about 300° to 350° C. in the autoclave in the presence of excess alkali. The free Guerbet fatty acids were obtained by decomposition of the produced sodium salts with dilute mineral acid.

IV. Guerbet fatty acid $C_{28}$

Acid number—130
Saponification number—131.5
Iodine number—1.98
Dripping point—51° C.

V. Guerbet fatty acid $C_{32/36}$

Acid number—116
Saponification number—121
Iodine number—4
Dripping point—63° C.

VI. Guerbet fatty acid $C_{44}$

Acid number—92
Saponification number—93.7
Iodine number—2.4
Dripping point—65° C.

Preparation of Beeswax Substitute Products

For the preparation of the beeswax substitute products, the above-mentioned Guerbet fatty acids were melted together with the other components at approximately 65° C. The following combinations were prepared:

VII. Combination with Guerbet fatty acid $C_{28}$

| Component | Parts by weight |
| --- | --- |
| Guerbet fatty acid $C_{28}$ | 15 |
| Cetyl palmitate | 30 |
| Glyceryl tripalmitate | 10 |
| Glyceryl monohydroxystearate | 25 |
| 12-Hydroxystearic acid | 20 |

VIII. Combinations with Guerbet fatty acid $C_{32/36}$

| Component | Parts by weight | | |
| --- | --- | --- | --- |
| | (a) | (b) | (c) |
| Guerbet fatty acid $C_{32/36}$ | 5 | 10 | 5 |
| Cetyl palmitate | 25 | 30 | 30 |
| Glyceryl trihydroxystearate | 10 | 10 | 15 |
| Glyceryl monohydroxystearate | 30 | 30 | 40 |
| 12-Hydroxystearic acid | 10 | 20 | 10 |
| Mikrowachs HP 67 (microwax) | 20 | — | — |

IX. Combinations with Guerbet fatty acid $C_{44}$

| Component | Parts by Weight |
| --- | --- |
| Guerbet fatty acid $C_{44}$ | 5 |
| Cetyl palmitate | 15 |
| Glyceryl tripalmitate | 20 |
| Glyceryl monohydroxystearate | 20 |
| Palmitic acid | 10 |
| Mikrowachs HP 67 (microwax) | 30 |

The composition of Example VIIIa and Beeswax DAB 7 were analyzed, the results being set forth in the following table:

TABLE 1

|  | Example VIIIa | Beeswax DAB 7 |
| --- | --- | --- |
| Acid number | 22.4 | 17–24 |
| Saponification number | 109 | 83–106 |
| Iodine number | 4.5 | — |
| Peroxide number | 3 | — |
| Rising melting point | 64° C. | 61°–66° C. |

Preparation of Cosmetic Preparations

The following cosmetics preparations were prepared in the usual manner, using Example VIII(a), with microwax, in comparison with white beeswax, and then tested for structure, consistency, and shelf-life. No differences were observed between the products containing the beeswax substitute according to the invention and those prepared with white beeswax.

X. Water-in Oil Skin Cremes

|  | Percent by weight | |
| --- | --- | --- |
| Component | (a) | (b) |
| Mixture of higher-molecular esters (Dehymuls E)® | 7.0 | 7.0 |
| Composition of Example VIII(a) | 3.0 | — |
| Beeswax, white | — | 3.0 |
| Decyl ester of oleic acid | 6.0 | 6.0 |
| Vaseline, white | 12.0 | 12.0 |
| Paraffin oil, viscous | 6.0 | 6.0 |
| Magnesium sulfate-7-hydrate | 0.3 | 0.3 |
| Glycerine, 86%, DAB 7 | 5.0 | 5.0 |
| Water | 60.7 | 60.7 |
|  | 100.0 | 100.0 |
| Structure and consistency after 6 months | smooth/soft | smooth/soft |
| Stability after 10 weeks: | | |
| at room temperature | stable | stable |
| at 40° C. | stable | stable |
| at −6° C. | stable | stable |

XI. Oil-in-Water Emulsions

|  | Percent by weight | |
| --- | --- | --- |
| Component | (a) | (b) |
| Mixture of mono-and di-glycerides of palmitic and stearic acid (Cutina MD)® | 4.0 | 4.0 |
| Stearic acid | 8.0 | 8.0 |
| Cetylstearyl alcohol with 12 mols of ethylene oxide | 1.5 | 1.5 |
| Cetylstearyl alcohol with 20 mols of ethylene oxide | 1.5 | 1.5 |
| 2-Octyldodecanol | 15.0 | 15.0 |
| Composition of Example VIII(a) | 2.0 | — |
| Beeswax, white | — | 2.0 |
| Paraffin oil, viscous | 20.0 | 20.0 |
| Triethanolamine | 0.2 | 0.2 |
| Water | 47.8 | 47.8 |
|  | 100.0 | 100.0 |
| Structure and consistency: | smooth/soft | smooth/soft |
| Stability after 4 weeks: | | |
| at room temperature | stable | stable |
| at 40° C. | stable | stable |

| Components | Parts by weight | |
| --- | --- | --- |
| Basic lipstick mass with 5% by weight of composition of Example VIII(a) | 72 | — |
| Basic lipstick mass with 5% by weight of beeswax white | — | 72 |
| Caprylic/capric acid triglyceride | 18 | 18 |
| Color pigment | 4.5 | 4.5 |
| Gold pigment | 5.5 | 5.5 |
|  | 100.0 | 100.0 |
| Application by rubbing | good | good |
| Rising melting point | 70° C. | 73° C. |
| Stability after 6 weeks: | | |
| at room temperature | no separation of oil | |
| at 50° C. | no separation of oil | |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A substitute beeswax composition comprised of:
   (a) from about 3 to 15% by weight, based on the weight of the total composition, of α-branched, aliphatic monocarboxylic acids of the general formula

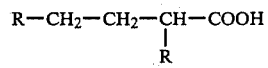

$$R-CH_2-CH_2-CH-COOH$$
$$\quad\quad\quad\quad\quad\quad\quad |$$
$$\quad\quad\quad\quad\quad\quad\quad R$$

in which R represents a linear alkyl radical with from about 12 to 20 carbon atoms;
   (b) from about 15 to 30% by weight of esters of fatty alcohols of chain lengths of $C_{12}$–$C_{22}$ and fatty acids of chain lengths of $C_{14}$–$C_{22}$;
   (c) from about 5 to 20% by weight of triglycerides of palmitic, stearic, hydroxystearic, or behenic acid;
   (d) from about 20 to 40% by weight of mono- and/or diglycerides of palmitic, stearic, hydroxystearic, or behenic acid;
   (e) from about 5 to 20% by weight of fatty acids or hydroxy fatty acids of chain lengths $C_{16}$–$C_{22}$; and
   (f) from 0 to about 30% by weight of microcrystalline paraffins having a melting range of from 70° to 72° C.

2. The composition of claim 1 which comprises from about 3 to 8% by weight of the α-branched, aliphatic monocarboxylic acids of component (a).

3. The composition of claim 1 wherein in the α-branched, aliphatic monocarboxylic acids of component (a), R represents a linear alkyl radical of from about 14 to 16 carbon atoms.

4. The composition of claim 1 wherein the fatty alcohols of component (b) have chain lengths of $C_{14}$–$C_{20}$.

5. The composition of claim 1 wherein the fatty acids of component (b) have chain lengths of $C_{16}$–$C_{20}$.

6. The composition of claim 1 comprising:
   (a) from about 3 to 8% by weight of the α-branched, aliphatic monocarboxylic acids;
   (b) from about 20 to 30% by weight of esters of fatty alcohols of chain lengths $C_{14}$–$C_{20}$ and fatty acids of chain lengths $C_{16}$–$C_{20}$;
   (c) from about 10 to 15% by weight of triglycerides of palmitic, stearic, or hydroxystearic acid;
   (d) from about 20 to 40% by weight of monoglycerides of palmitic, stearic, or hydroxystearic acid;
   (e) from about 10 to 20% by weight of fatty acids or hydroxy fatty acids of chain lengths $C_{18}$–$C_{20}$; and (f) from about 10 to 20% by weight of microcrystalline paraffins having a melting range of from 70° to 72° C.

7. The composition of claim 1, which comprises:
(a) about 5% by weight of α-branched, aliphatic monocarboxylic acids, in which R represents a linear alkyl radical with from about 14 to 16 carbon atoms;
(b) about 25% by weight of cetyl palmitate;
(c) about 10% by weight of glyceryl trihydroxystearate;
(d) about 30% by weight of glyceryl monohydroxystearate;
(e) about 10% by weight of 12-hydroxystearic acid; and
(f) about 20% by weight of microcrystalline paraffin having a melting range of from about 70° to 72° C.

8. A cosmetic agent for the care and protection of the skin of warm-blooded animals comprising from 1 to 50% by weight, relative to the total agent, of a beeswax substitute composition of claim 1 and the remainder conventional cosmetic excipients.

* * * * *